United States Patent [19]

Doi

[11] Patent Number: 4,716,288

[45] Date of Patent: Dec. 29, 1987

[54] SECURITY DEVICE FOR DETECTING DEFECTS IN TRANSMITTING FIBER

[75] Inventor: Yuzuru Doi, Tokyo, Japan

[73] Assignee: Asahi Kogaku Kogyo Kabushiki Kaisha, Tokyo, Japan

[21] Appl. No.: 847,137

[22] Filed: Apr. 2, 1986

Related U.S. Application Data

[63] Continuation of Ser. No. 316,385, Oct. 29, 1981, abandoned.

[30] Foreign Application Priority Data

Nov. 1, 1980 [JP] Japan .................................. 55-154328

[51] Int. Cl.⁴ ........................................... G01N 21/88
[52] U.S. Cl. .................................. 250/227; 128/303.1; 356/73.1
[58] Field of Search .............................. 356/73.1, 237; 128/303.1; 250/227

[56] References Cited

U.S. PATENT DOCUMENTS 3,981,592 9/1976 Williams .............................. 356/237

FOREIGN PATENT DOCUMENTS 2023004 12/1979 United Kingdom ............. 128/303.1

Primary Examiner—Vincent P. McGraw
Attorney, Agent, or Firm—Sughrue, Mion, Zinn, Macpeak & Seas

[57] ABSTRACT

An apertured reflection plate obliquely oriented with respect to a fiber optical axis allows light to be introduced through the aperture to a condenser lens for introduction to the fiber. Light reflected from the exit face of the fiber will come out of the entrance end face, be spread by the lens and be reflected by the outer regions of the reflection plate to a light detecting element. In response to an abnormal detection signal, the laser can be disabled.

16 Claims, 3 Drawing Figures

SECURITY DEVICE FOR DETECTING DEFECTS IN TRANSMITTING FIBER

This ia a continuation, of application Ser. No. 316,385 filed Oct. 29, 1981, now abandoned.

BACKGROUND OF THE INVENTION

This invention relates to a damage detecting device for a laser power transmitting fiber. The invention is intended to detect damage in an optical fiber adapted to transmit a medical laser beam, to prevent the occurrence of various hazards due to the damage and thereby improve the security of a medical laser scalpel.

In general, a high power laser beam is introduced to a transmitting fiber used for a medical laser scalpel. If dust in the air sticks to the entrance end face or the exit end face of the fiber, or the exit end face is contaminated by filth, or materials evaporated from or broken off from an object to which the laser beam is applied stick to the end portion of the transmitting fiber, the energy of the laser beam may be concentrated on the particulate matter so that the entrance end face or the exit end face of the fiber are damaged by heat. This trouble has been experienced frequently. Furthermore, the transmitting fiber may also be broken by careless handling.

If, under this condition, the operation is continued, the necessary amount of energy may not be applied to the object, and it may not be possible to satisfactorily machine or to sufficiently treat a diseased part. In addition, since the energy is concentrated at the damaged part of the fiber, the mechanisms around the damaged part may be damaged or broken by heat, which is hazardous to the operator.

Heretofore, the above-described damage of the transmitting fiber or the breakage of the transmitting fiber due to physical impact have been detected by observing the scattered light, at the exit part of the fiber, of the guide light beam which is introduced along the optical axis of the laser beam. However, the scattering condition of the guide light beam, which is caused by the defective end portion of the fiber, is greatly affected by the ambient light, and therefore it is considerably difficult to determine the damage or defects by observing the scattered light at the exit part of the fiber. Especially in a medical laser knife, the ability to increase the intensity of the guide light beam is limited because increasing this intensity may make it more difficult for the operator to see what he is doing, with the result that the diseased part being irradiated by the laser beam may be damaged by the wandering laser beam. Furthermore, if the operator must pay attention to the occurrence of damage in the fiber while working, his working efficiency will be greatly reduced.

In another conventional method, a conductor is arranged along the transmitting fiber or the sheath of the transmitting fiber, and the conductor thus arranged is connected to a detector to detect breakage or damage. However, this method is capable of detecting damage only in the side surfaces, and almost all damage to transmitting fibers first occurs due to heat at the entrance end faces or the exit end faces. Therefore, the damaged entrance or exit end face of the fiber cannot be sufficiently detected by this method.

SUMMARY OF THE INVENTION

In view of the foregoing, an object of this invention is to provide a damage detecting device which can immediately detect the occurrence of damage in transmitting fibers.

Briefly, this is achieved according to the present invention by a detecting device which measures the amount of light reflected back to the entrance of the optical fiber from the end face thereof. If the end face is damaged, the reflected light will decrease, and the laser beam can be blocked by an automatically operated shutter.

DESCRIPTION OF THE PREFERRED EMBODIMENTS

Figure 1:
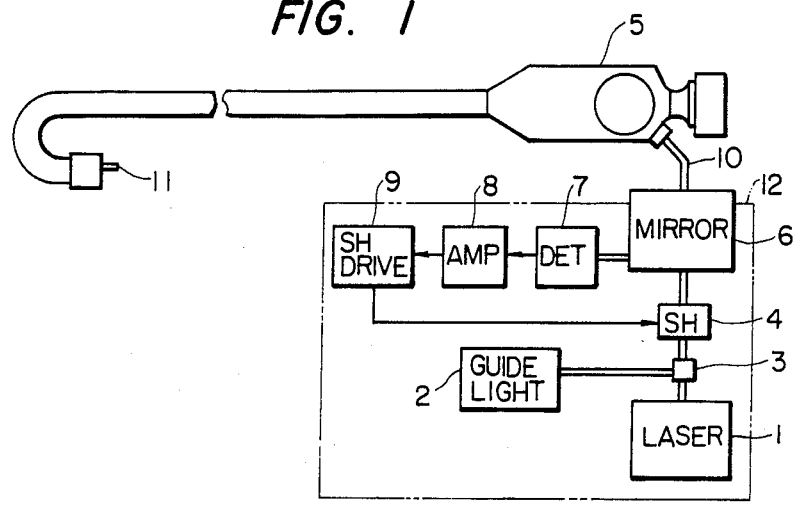
FIG. 1 is a schematic diagram (partly as a block diagram) showing a damage detecting device according to this invention, as applied to a medical laser scalpel.

FIG. 1 is a schematic diagram showing the damage detecting device according to this invention, which is applied to a medical laser scalpel.

As is well known in the art, in a conventional ordinary device of this type, an irradiating light source 1 such as an Nd:YAG laser or a $CO_2$ laser, and a guide light source 2 such as a He-Ne laser or a xenon lamp are provided separately, and a half-mirror 3 is provided on the optical axis of the irradiating light source 1 so that the guide light source 2 and the irradiating light source 1 have a common optical axis. A shutter 4 is provided on the optical axis, and can be operated to block the laser beam when the laser beam, etc. malfunctions. Furthermore, it is well known in the art that various mechanisms are available to operate the shutter 4 when such a malfunction occurs, as was described with reference to the prior art. In this invention, the malfunction detecting device operating in association with the shutter 4 is provided between an endoscope 5 and the shutter 4. The detecting device comprises: a mirror 6 provided on the aforementioned optical axis; an optical detector 7 provided on the axis of the light reflected from the mirror 6; an amplifier circuit 9 coupled to the detector 7; and a shutter drive circuit 9 coupled to the amplifier circuit 8, to operate the shutter 4.

Further in FIG. 1, reference numeral 10 designates the power laser fiber; 11, the exit end face of the fiber 10; and 12, a chassis in which the light sources, the detecting device, etc. are incorporated. The entrance end face and the exit end face of the fiber 10 are not coated, but are subjected to optical polishing in order to improve their reflectivity.

Figure 2:
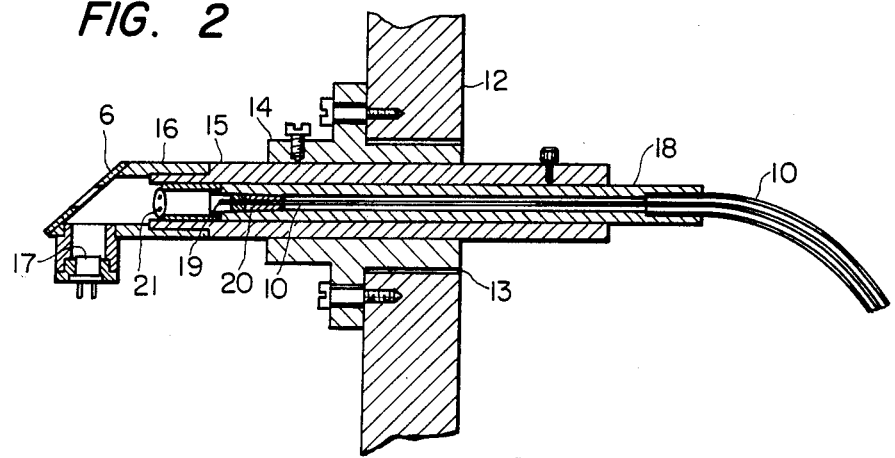
FIG. 2 is a sectional view showing the essential components of the damage detecting device according to this invention.

FIG. 2 is a sectional view showing one example of the entrance part of the fiber 10 according to this invention. A cylindrical mounting member 14 is fixedly inserted into a hole 13 cut in the chassis 12. A cylindrical guide pipe 15 is slidably fitted in the mounting member 14. The end portion of the guide pipe 15, which is protruded inside the chassis 12, is threaded, and a light receiving section holder 16 is detachably connected to the end portion thus threaded. A mirror 6 with a holder is bonded to the other end of the holder 16 in such a manner that it forms a 45° angle with the optical axis. A light receiving element 17 such as a photo-transistor or a photo-diode is fixedly provided at a position perpendicular to the optical axis of the fiber. A thin slide piece 18 is slidably fitted in the guide pipe 15. The entrance end portion of the fiber 10 is inserted into the slide pipe 18. In the entrance end portion thus inserted, a fixing member 20 and a condenser lens 21 are incorporated near the entrance end face 19. The light receiving element 17 is connected to the optical detector 7.

In operation, a laser beam emitted by the irradiating light source 1 and a guide beam emitted by the guide light source 2 advance along the same optical axis. Therefore, the beams are applied through the condenser lens 21 to the entrance end face 19 of the fiber 10, thus emerging from the exit end face 11 to irradiate the diseased part. Since the exit end face 11 of the fiber 10 is merely optically polished, the reflection factor for the laser beam or the guide beam is somewhat high. Therefore, a part of the light is reflected by the exit end face 11 back to the entrance end face, thus emerging from the entrance end face 19. In this operation, the reflected light emerges with a relatively divergent angle by means of the condenser lens 21. The reflected light is further reflected by the mirror 6, which has a hole therein and is then applied to the light receiving element 17. The variation of the reflected light is detected by the optical detector 7.

Figure 3:
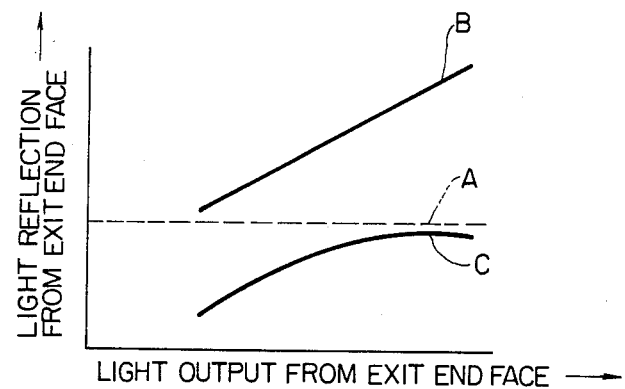
FIG. 3 is a graphical representation indicating the reflection characteristics of the exit end face of a laser fiber.

In the case where, for instance, the exit end face 11 is damaged by heat or the end portion is broken, the reflected light can be detected for abnormality by setting the optical detector 7 as described below. This detection method will be described with reference to FIG. 3. In FIG. 3, a line A indicates a set level, a line B indicates the reflection characteristic of a normal fiber, and a curve C indicates the reflection characteristic of an abnormal fiber. As is apparent from the graphical representation in FIG. 3, in the case of the line B (or when the fiber is normal) the amount of reflection is larger than the set level A. In this case, the output of the detector circuit 7 is applied through the amplifier circuit 8 to the shutter control circuit 9 to maintain the shutter 4 open. When the entrance end face 19 becomes abnormal, for instance, by being shifted from the optical axis or by being contaminated, the laser beam is not reflected from the exit end face 11 at all, or at least the amount of reflected light is greatly reduced. Therefore, the detected reflection light will be shown by curve C, and the shutter 4 will be closed.

The malfunction detecting device of this invention arranged as described above can instantly detect damage to the entrance or exit end face of the transmitting fiber, and can also detect damage to the periphery of the fiber itself since this will affect the internal reflection of the fibers. Thus, further damage due to continued laser irradiation can be prevented. Since the damage detecting device is considerably simple in construction, it is unnecessary to greatly modify the entrance part of the conventional laser fiber, which reduces the manufacturing cost. When the detecting device is applied to an industrial machining apparatus or a medical laser scalpel, safety is positively maintained, and the advantages of the invention in practical use should be highly appreciated.

What is claimed is:

1. In a laser machining or medical instrument wherein a laser irradiating light beam and a guide light beam are introduced into an optical fiber through an entrance end face thereof, are transmitted along said optical fiber and exit said optical fiber from an exit end face thereof, fault detecting means comprising:

light detecting means for detecting the amount of light reflected back toward said entrance end face by interior surfaces of said optical fiber, laser cutoff means, and drive means for actuating said laser cutoff means when the amount of light detected by said light detecting means varies from a predetermined value determined accordance with the amount of reflection normally caused at said fiber exit end face.

2. A fault detecting means as claimed in claim 1, wherein said light detecting means is disposed near said entrance end face.

3. A fault detecting means as claimed in claim 1 or 2, wherein said light detecting means provides an output signal comprising an abnormal detection signal when an abnormal amount of reflected light is detected, said laser cutoff means comprising disabling means for stopping the introduction of at least said laser irradiating beam into said entrance end face.

4. A fault detecting means as claimed in claim 3 wherein said disabling means comprises a shutter driven by said drive means.

5. A fault detecting means as claimed in claim 3, wherein said abnormal detection signal is provided when the amount of detected reflection light is below a predetermined level.

6. A fault detecting means as claimed in claim 2, wherein said light detecting means comprises:
a condenser lens adjacent said entrance end face;
a reflection member having a reflection surface which is directed toward said condenser lens, which reflection surface is disposed obliquely with respect to the optical axis of said fiber at said entrance end face, said reflection member having an aperture therein through which said irradiating and guide light beams are provided through said condenser lens to said entrance end face; and
a light detecting element for detecting said reflected light which passes from said entrance end face through said condenser lens to strike said reflection surface.

7. A fault detecting means as claimed in claim 6, wherein said condenser lens increases the divergent angle of light passing from said entrance end face to said reflection surface.

8. A fault detecting means as claimed in claim 6, wherein said reflection surface forms a substantially 45° angle with both said light detecting element and said fiber optical axis at said entrance end face.

9. A fault detecting means as claimed in claim 2, wherein said laser device is an endoscope.

10. A fault detecting means as claimed in claim 1, wherein said fiber exit end face comprises an optically polished, uncoated surface.

11. A fault detecting means as claimed in claim 1, wherein said laser device is a surgical laser knife.

12. A fault detecting means as claimed in claim 1, further comprising a first tubular guide element housing said optical fiber and including a lens fitted in an end portion thereof.

13. A fault detecting means as claimed in claim 12, further comprising a second tubular guide element surrounding and housing said first tubular guide element, for detachably mounting a detection assembly comprising a reflecting mirror and a photosensitive element.

14. A fault detecting means as claimed in claim 13, further including means for mounting said second tubular guide element to a chassis incorporating sources of said laser light beam and said guide light beam, said reflecting mirror, said photosensitive element, said laser cutoff means and said drive means.

15. A laser surgical knife, comprising:

a first laser generating a medical laser beam;

a second laser light source for generating a guide light beam;

an optical fiber having entrance and exit ends;

means for rendering coaxial said medical laser beam and said guide light beam, and means for introducing both said beams into said optical fiber at said entrance end thereof;

detecting means for detecting the quantity of light reflected back toward said entrance end face by internal surfaces of said optical fiber; and means for intercepting at least said medical laser beam at a point prior to introduction into said optical fiber, in response to the detection by said detecting means of a lower than normal quantity of reflected light.

16. A laser cutting apparatus, comprising:

a first laser light source for generating a laser cutting beam;

a second laser light source for generating a guide light beam;

an optical fiber having entrance and exit ends;

means for rendering coaxial said laser cutting beam and said guide light beam, and means for introducing both said beams into said optical fiber at said entrance end thereof;

detecting means for detecting the quantity of light reflected back toward said entrance end face by internal surfaces of said optical fiber; and means for intercepting at least said laser cutting beam at a point prior to introduction into said optical fiber, in response to the detection by said detecting means of a lower than normal quantity of reflected light.

* * * * *